(12) United States Patent
Benvegnu et al.

(10) Patent No.: US 10,544,180 B2
(45) Date of Patent: Jan. 28, 2020

(54) PROCESS FOR PREPARING COMPOSITIONS COMPRISING ALKYL(ALKYL-GLUCOSIDE)URONATES, SAID COMPOSITIONS AND USE THEREOF AS A SURFACTANT

(71) Applicant: École Nationale Supérieure de Chimie, Rennes (FR)

(72) Inventors: Thierry Benvegnu, Rennes (FR); Freddy Pessel, Merlevenez (FR); Maud Benoît, Ploubazlanec (FR); Yves Lelong, Plouezec (FR)

(73) Assignee: ÉCOLE NATIONALE SUPÉRIEURE DE CHIMIE, Rennes (FR)

( * ) Notice: Subject to any disclaimer, the term of this patent is extended or adjusted under 35 U.S.C. 154(b) by 0 days.

(21) Appl. No.: 16/061,181

(22) PCT Filed: Dec. 9, 2016

(86) PCT No.: PCT/FR2016/053291
§ 371 (c)(1),
(2) Date: Nov. 13, 2018

(87) PCT Pub. No.: WO2017/098175
PCT Pub. Date: Jun. 15, 2017

(65) Prior Publication Data
US 2019/0062360 A1    Feb. 28, 2019

(30) Foreign Application Priority Data

Dec. 11, 2015 (FR) ..................... 15 62232

(51) Int. Cl.
*C07H 1/00* (2006.01)
*C07H 15/04* (2006.01)
*C11D 1/66* (2006.01)
*A61K 8/60* (2006.01)
*A61Q 19/00* (2006.01)
*A61K 8/06* (2006.01)

(52) U.S. Cl.
CPC ............. *C07H 1/00* (2013.01); *A61K 8/06* (2013.01); *A61K 8/604* (2013.01); *A61Q 19/00* (2013.01); *C07H 15/04* (2013.01); *C11D 1/662* (2013.01); *A61K 2800/10* (2013.01); *A61K 2800/805* (2013.01)

(58) Field of Classification Search
CPC ........................................... C07H 1/00
USPC ........................................... 549/417
See application file for complete search history.

(56) References Cited

U.S. PATENT DOCUMENTS 5,147,861 A    9/1992    della Valle et al.

FOREIGN PATENT DOCUMENTS

| EP | 0537820 A2 | 4/1993 |
|---|---|---|
| EP | 0635516 A1 | 1/1995 |
| EP | 0819698 A2 | 1/1998 |
| WO | WO03/099870 A2 | 12/2003 |
| WO | WO03/104248 A2 | 12/2003 |

OTHER PUBLICATIONS

Ikeda, A., et al., "Preparation of low-molecular weight alginic acid by acid hydrolysis," Carbohydrate Polymers 2000;42(4):421-425.
Macher, I., et al., "Methyl α- and β-L-gulofuranosidurano-6,3-lactone," Carbohydrate Res. 1979;77:225-230.
International Search Report and Written Opinion for PCT Patent App. No. PCT/FR2016/053291 (dated Feb. 16, 2017) with English translation of ISR.

*Primary Examiner* — Taofiq A Solola
(74) *Attorney, Agent, or Firm* — Kenealy Vaidya LLP (57) ABSTRACT

Some embodiments relate to a novel process for preparing compositions including alkyl(alkyl-glucoside)uronates, from biobased or biocompatible/biodegradable raw materials, and also salts and acids thereof.

20 Claims, 3 Drawing Sheets

PROCESS FOR PREPARING COMPOSITIONS COMPRISING ALKYL(ALKYL-GLUCOSIDE)URONATES, SAID COMPOSITIONS AND USE THEREOF AS A SURFACTANT

CROSS REFERENCE TO RELATED APPLICATIONS

This application is a national phase filing under 35 C.F.R. § 371 of and claims priority to PCT Patent Application No. PCT/FR2016/053291, filed on Dec. 9, 2016, which claims the priority benefit under 35 U.S.C. § 119 of French Patent Application No. 1562232, filed on Dec. 11, 2015, the contents of each of which are hereby incorporated in their entireties by reference.

BACKGROUND to a novel process for preparing compositions including alkyl(alkyl guloside)uronates or a mixture of alkyl(alkyl guloside)uronates and of alkyl(alkyl mannoside)uronates, exclusively from starting materials which are biobased (alginates, oligoalginates, poly(oligo)guluronates, brown algae) or biocompatible/biodegradable, and also salts and acids thereof.

Some embodiments have for example applications in surfactants, in particular for cosmetics, the phytosanitary field, detergency and CPW (Construction and Public Works).

In the description below, the references between square brackets ([ ]) refer to the reference list presented at the end of the text.

100% biobased surfactants composed of a hydrophilic part and a lipophilic part, both of plant origin, represent approximately 5% to 10% of the total volumes of surfactants. Despite a strong potential in the cosmetics and detergency sectors and in phytosanitary products, they struggle to replace their equivalents of fossil origin. Price difference and a narrower application spectrum explain in particular this difference. The use of starting materials based on algal polysaccharides which are characterized by an original chemical functionality compared with polysaccharides from terrestrial plants, constitutes an approach that could make it possible to broaden the fields of application of the 100% biobased surfactants thus obtained.

Alginates, which are polysaccharides present in the cell wall of brown algae, include or consist of L-guluronic and D-mannuronic acids. While studies have already shown the possibility of exploiting D-mannuronic acid oligomers in the surfactant field, the preparation of compositions based on L-guluronic acid or on mixtures both of L-guluronic acid and of D-mannuronic acid in monomer form and making it possible to exploit all of the saccharides present in the biopolymer, have not been developed to date.

Glycoside surfactants constitute a large family of commercial biobased surfactants. They are surfactants of which the surface properties, the biodegradability and the innocuousness with respect to the skin provide them with many applications in the detergency, cosmetics and food sectors. Sugar-derived non-ionic surfactants are principally represented on the market by alkylpolyglucosides APGs (85 000 t/year), sorbitan esters (20 000 t/year), sucrose esters (<10 000 t/year) and methylglucosides (<10 000 t/year). Sugar-derived anionic surfactants are present on the market to a much smaller extent compared with their nonionic homologs ("Sugar-based Surfactants: fundamentals and applications", Surfactant science series vol.143, Ed. C. Carnero Ruiz, CRC Press Taylor & Francis Group, 2009 (ISBN 978-1-4200-5166-7)) [1]. This observation can in particular be explained by the difficulty in developing economically viable processes for the controlled introduction of one or more anionic functions onto the saccharide structure. In the carboxylate series, the strategies are based principally on the direct oxidation or esterification of the $C_6$—OH group of alkyl polyglycosides (APGs). An alkyl polyglucoside carboxylate, Plantapon LGC Sorb (INCI name sodium lauryl glucose carboxylate (and) lauryl glucoside) has been introduced onto the market by Cognis as a new anionic surfactant for applications in bodycare formulations. In shampoos and shower gels, it provides a better foaming capacity than the non-ionic surfactants. For bodycare products, it improves the sensory properties. An industrial process based on the reaction of sodium monochloroacetate in an aqueous solution of alkyl polyglycoside (without additional solvent) has been developed in this context (Behler et al., in Proceedings 6th World Surfactant Congress, CESIO June, Berlin, 2004) [2].

Currently, there are not many ways to obtain 100% biobased surfactants in the form of a non-ionic and anionic monomer from one and the same natural source. Surfactants derived from glycosiduronic acids have been produced in the glucu- and galacturonic series in the form of monomers and oligomers (patents EP 0 532 370 and U.S. Pat. No. 5,312,907, patent application FR 2 717 177, international application WO 93/02092) [3-6]. In the guluronic series, surfactants exist in the polymeric form, in particular in the form of modified alginate (international application WO 98/12228, patent U.S. Pat. No. 5,147,861) [7, 8]. Surfactants derived from (Alkyl-D-mannopyranoside)uronic acid have been produced in mono- and dimeric form from D-mannuronic acid oligomers (Benvegnu et al., Topics in Current Chemistry, 294: 143-164, 2010; Roussel et al., Eur. J. Org. Chem., 3085-3094, 2005; patent application FR 02/840306; international application WO 03/104248) [9-12]. The process is based on the production of saturated (acid depolymerization) and unsaturated (enzymatic depolymerization) oligomannuronates which are subsequently converted into monosaccharide and disaccharide intermediates including 2 (monosaccharide) or 4 (disaccharide) butyl chains. These synthons constitute key intermediates in the eco-compatible synthesis (without solvent, without waste, biodegradable reagents) of surfactant structures with a variable hydrophilic-hydrophobic balance, obtained by a process of transesterification/transglycosylation by variable-length fatty alcohols. These surfactants having identical lipophilic chains (two chains in the case of the monosaccharide) can subsequently be saponified in order to obtain anionic surfactants (a single chain in the case of the monosaccharide) including a carboxylic unit. These amphiphilic molecules cover several applications in the detergency and liquid crystal field.

International application WO 03/099870 [13] filed by CEVA relates to the preparation of oligomannuronic and oligoguluronic from fresh or dry algae. This process includes or consists of pre-extraction of the alginates, followed by numerous steps of precipitation by modulating the pH of the reaction medium in order to separate the G blocks and the M blocks constituting the alginates. Finally, an enzymatic or acid hydrolysis step produces the oligomannuronics or oligoguluronics.

SUMMARY

Some embodiments are directed to a process which addresses or overcomes some or all of these deficiencies, drawbacks and obstacles of the related art, in particular for a simple process which makes it possible to synthesize surfactant compositions directly from less refined starting materials, to reduce costs and to improve the properties expected in the surfactants field.

The applicants have developed a novel solvent-free process using biocompatible/biodegradable reagents, for directly and simply obtaining non-ionic and anionic compositions of L-guluronic acid derivatives or of mixtures of L-guluronic acid and D-mannuronic acid (monomer form) directly from oligoalginates, alginates which have been refined or semi-refined (mixture of alginate, of cellulose, of hemicellulose, of laminaran and of fucan). The poly(oligo) guluronates (or homopolymeric blocks of α-L-guluronic acid, partly in sodium salt form) come from the depolymerization of alginates according to the process described in international application WO 03/099870 [13]. The alginates and the oligoalginates are obtained by simple treatments in acidic aqueous media, from fresh or dry algae, for example obtained according to the protocol described in Example 2 below, according to the process of international application WO 98/40511 [15]. Simple treatments of partial purification of the reaction crudes (elimination of the salts and/or the residual fatty alcohols) or of isolation of the surfactant compositions result in derived compounds and in compositions having performance levels/characteristics appropriate to market needs.

Some embodiments are directed to a process for preparing a composition including:

(i) alkyl(alkyl guloside)uronates of formulae (Ia), (Ib) and (Ic):

or (ii) a mixture of alkyl(alkyl guloside)uronates of formulae (Ia), (Ib) and (Ic) and of alkyl(alkyl mannoside)uronates of formulae (IIa), (IIb) and (IIc):

wherein
$R_1$ is a linear or branched, saturated or unsaturated alkyl chain of from 2 to 22 carbon atoms;
$R_2$ is a hydrogen atom, $R_1$, an alkali metal atom, an alkaline-earth metal atom, or a quaternary ammonium group of formula (III):

wherein each of $R_3$ to $R_6$ is independently a hydrogen atom, an alkyl having from 1 to 6 carbon atoms or a hydroxyalkyl having from 1 to 6 carbon atoms, wherein the process includes:
a) hydrolysis of poly(oligo)guluronates, of oligoalginates, of alginates and/or brown algae;
b) esterification and glycosylation of the hydrolysate resulting from step a) with a linear or branched, saturated or unsaturated alcohol of formula ROH, having from 1 to 4 carbon atoms;
c) trans-esterification and trans-glycosylation of the reaction medium resulting from step b) with a linear or branched, saturated or unsaturated alcohol of formula R'OH having from 2 to 22 carbon atoms; and
d) neutralization of the reaction medium resulting from step c) in the presence of water and of a base $M(OH)_x$ in which M is an alkali metal or alkaline-earth metal, and x is the valency.

The non-ionic and anionic compositions contain, in a novel manner, in the form of a monomer, derivatives of L-guluronic acid or of the two uronic acids (L-guluronic acid and D-mannuronic acid) derived from the same polysaccharide and, in some cases, hexoses and pentoses derived from other polysaccharides present in the algal extract (cellulose, hemicellulose, laminaran, fucan: in the case of semi-refined alginates as starting material).

For the purposes of some embodiments, the term "poly (oligo)guluronates" is intended to mean homopolymeric blocks of α-L-guluronic acid partly in sodium salt form, resulting from the depolymerization of alginates, for example according to the process of international application WO 03/099870 [13].

For the purposes of some embodiments, the term "oligoalginates" is intended to mean the products resulting from an enzymatic and/or acid treatment of alginate, which are for example obtained according to the protocol described in Example 2 below, according to the process of international application WO 98/40511 [15].

For the purposes of some embodiments, the term "alginates" is intended to mean refined and/or semi-refined alginates, for example obtained according to the protocol described in Example 2 below. It is also intended to mean bacterial alginates obtained, for example, from culture of mucoid bacteria (e.g. cf. international application WO 2009/134368) [14].

For the purposes of some embodiments, the term "brown algae" is intended to mean the algae called *Phaeophyceae*, of which there are 1500 species (e.g. *Ascophyllum nodosum, Fucus serratus, Laminaria hyperborea, Laminaria digitate, Ecklonia maxima, Macrocystis pyrifera, Sargassum vulgare,* etc. . . . ), and the walls of which are essentially composed of sulfated fucans and of alginate.

For the purposes of some embodiments, the term "ionic solvent" is intended to mean, for example, 1-butyl-3-methylimidazolium chloride [BMIM]Cl, 1-butyl-3-methylimidazolium bromide [BMIM]Br, tris-(2-hydroxyethyl)methylammonium methylsulfate (HEMA) and 1-ethyl-3-methylimidazolium acetate [EMIM]AcO; the ionic solvent typically including up to 10% of water.

For the purposes of some embodiments, the term "eutectic solvent" is intended to mean systems formed from a eutectic mixture of Lewis or Brönsted bases or acids which may contain a variety of anionic species and/or cationic species. The first-generation eutectic solvents were based on mixtures of quaternary ammonium salts with hydrogen-bond donors such as amines or carboxylic acids (e.g. quaternary ammonium salt and metal chloride (hydrate)).

According to one particular embodiment, the process includes, before step a), the steps of preparation of the (semi-)refined alginates, oligoalginates and poly(oligo)guluronates. The poly(oligo)guluronates come from the depolymerization of alginates. The semi-refined alginates come from the acid leaching of brown algae, followed by dissolution of the sodium alginates by increasing the pH, then by solid/liquid separation in order to remove the algal residues. The refined alginates come from an additional step of depigmentation with formol and from a purification step. The oligoalginates come from the enzymatic and/or acid treatment of alginate solution.

According to one particular embodiment:
(i) in the case of alginates ("separate mode"), the step of esterification and glycosylation b) of the reaction medium resulting from step a) is carried out after step a) due to insufficient solubility of the polysaccharides in an aqueous medium containing a short-chain alcohol (1 to 4 carbon atoms);
(ii) in the case of the poly(oligo)guluronates or of the oligoalginates, steps a) and b) are carried out in the same time ("combined mode") due to the sufficient solubility of these starting materials in a medium including or consisting essentially of water and a short-chain alcohol (1 to 4 carbon atoms).

According to one particular embodiment, for the alginates, step a) is carried out in the presence (i) of water and/or of an ionic solvent and/or of a eutectic solvent, and (ii) of an acid catalyst such as, for example, hydrochloric acid, sulfuric acid, an alkylsulfuric acid such as decyl or lauryl sulfuric acid, a sulfonic acid such as benzenesulfonic acid, para-toluenesulfonic acid or camphorsulfonic acid, an alkylsulfonic acid such as methanesulfonic (or methylsulfonic) acid, decylsulfonic acid, laurylsulfonic acid or sulfosuccinic acid, or an alkyl sulfosuccinate such as decyl sulfosuccinate or lauryl sulfosuccinate, perhalohydric acids, such as perchloric acid, or metals such as iron, oxides thereof or salts thereof, such as halides thereof. Advantageously or preferably, it is alkylsulfonic acid or methanesulfonic acid.

Step a) in "separate mode" is carried out distinctly from step b), for example by bringing into contact 1 equivalent of refined or semi-refined alginates obtained from the species *Ascophyllum, Durvillaea, Ecklonia, Laminaria, Lessonia, Macrocystis, Sargassum* and *Turbinaria*, and advantageously or preferably alginates obtained from the *Laminaria* species, preferentially from the species *Laminaria digitata*, the weight composition of which is, for the refined alginate: solids 94.2%/crude, mineral matter 37.2% dry/dry, uronic acids (D-mannuronic and L-guluronic) 67.5% dry/dry, and for the semi-refined alginate: solids 94.9%/crude, mineral matter 47.0% dry/dry, uronic acids (D-mannuronic and L-guluronic) 29.1% dry/dry, glucose 10.9% dry/dry, fucose 2.1% dry/dry, xylose <0.5% dry/dry; from 10 to 1000 equivalents by weight of water, advantageously or preferably 30 equivalents by weight; from $10^{-3}$ to 10 molar equivalents of an acid catalyst as defined above, and advantageously or preferably from 1.1 to 10 molar equivalents of alkylsulfonic acid, and advantageously or preferably 5 molar equivalents of methanesulfonic acid. This (semi-)refined alginate hydrolysis step is preferentially heated between 80° C. and 130° C., and advantageously or preferably brought to the reflux of water at atmospheric pressure over the course of a reaction time that can be from 1 to 24 hours and advantageously or preferably over the course of a reaction time of 8 hours.

The step of esterification and glycosylation b) of the reaction medium resulting from step a) in "separate mode" is then carried out at atmospheric pressure and at the boiling point of water or of the azeotrope formed with a linear or branched, saturated or unsaturated alcohol ROH having from 1 to 4 carbon atoms. Advantageously or preferably, the alcohol ROH is n-butanol.

This esterification and glycosylation step b) is carried out, for example, by introducing from 2 to 300 molar equivalents of alcohol, and advantageously or preferably 150 molar equivalents, into the reaction medium resulting from step a) carried out in the presence of (semi-)refined alginates. The reaction is then carried out at the reflux of the azeotrope at atmospheric pressure (Dean Stark apparatus), between 130 and 140° C. in the case of butanol, advantageously or preferably over the course of 7 or 15 hours, the time that may be required for virtually all of the water to be eliminated. The crude reaction medium is then cooled to ambient temperature.

According to one particular embodiment, for the poly (oligo)guluronates and the oligoalginates, steps a) and b) are carried out at the same time, in the presence (i) of water and/or of an ionic solvent and/or of a eutectic solvent, (ii) of a short-chain alcohol (1 to 4 carbon atoms) such as, for example, n-butanol, and (iii) of an acid catalyst such as, for example, hydrochloric acid, sulfuric acid, an alkylsulfuric acid such as decyl or lauryl sulfuric acid, a sulfonic acid such as benzenesulfonic acid, para-toluenesulfonic acid or camphorsulfonic acid, an alkylsulfonic acid such as methanesulfonic (or methylsulfonic) acid, decylsulfonic acid, laurylsulfonic acid or sulfosuccinic acid, or an alkyl sulfosuccinate such as decyl sulfosuccinate or lauryl sulfosuccinate, perhalohydric acids, such as perchloric acid, or metals such as iron, oxides thereof or salts thereof, such as halides thereof. Advantageously or preferably, it is alkylsulfonic acid or methanesulfonic acid.

Steps a) and b) in "combined mode" are carried out, for example, by bringing into contact 1 equivalent of poly (oligo)guluronates or oligoalginates obtained from the species such as *Ascophyllum, Durvillaea, Ecklonia, Laminaria, Lessonia, Macrocystis, Sargassum* and *Turbinaria*; from 0.1 to 100 equivalents by weight of water, advantageously or preferably 2 equivalents by weight; from 2 to 300 molar equivalents of alcohol such as n-butanol, advantageously or preferably 150 molar equivalents; from $10^{-3}$ to 10 molar equivalents of an acid catalyst as defined above, and advantageously or preferably from 1.1 to 10 molar equivalents of alkylsulfonic acid, and advantageously or preferably 2.2 molar equivalents of methanesulfonic acid. The reaction is then carried out at the reflux of the azeotrope at atmospheric pressure (Dean Stark apparatus), between 130 and 140° C. in the case of butanol, advantageously or preferably over the course of 7 or 15 hours, the time that may be required for virtually all of the water to be eliminated. The crude reaction medium is then cooled to ambient temperature.

The composition thus formed at the end of steps a) and b) carried out in separate or combined mode includes or consists predominantly of compounds including two chains originating from the alcohol (advantageously or preferably from butanol), derived from L-guluronic acid (starting from poly(oligo)guluronates) or derived from the mixture of L-guluronic acid and D-mannuronic acid (starting from oligoalginates or (semi-)refined alginates).

According to one particular embodiment of, the preparation of a composition including L-guluronic acid derivatives or a mixture of derivatives of L-guluronic acid and of D-mannuronic acid, in which the alkyl chain is longer, is continued by a trans-esterification and trans-glycosylation step c) carried out on this composition including or consisting predominantly of the double-stranded compound and resulting from step b), in the presence of a linear or branched, saturated or unsaturated alcohol of formula R'OH, in which R' is composed of from 2 to 22, advantageously or preferably from 8 to 18, preferentially from 12 to 18, carbon atoms. For example, the alcohol R'OH is chosen from the group include or consisting of saturated or unsaturated, linear fatty alcohols such as dodecanol and oleyl alcohol. This trans-esterification and trans-glycosylation step c) is carried out, for example, by introducing, into the reaction medium resulting from step b) (with as starting material the poly(oligo)guluronates, the oligoalginates) from 2 to 50 molar equivalents of an alcohol of formula R'OH as defined above, and advantageously or preferably 4 molar equivalents; from $10^{-3}$ to 10 molar equivalents of an acid catalyst as defined above, and advantageously or preferably from 0.1 to 10 molar equivalents of alkylsulfonic acid, and advantageously or preferably 1 molar equivalent of methanesulfonic acid. This trans-esterification and trans-glycosylation step c) is carried out, for example, by introducing, into the composition resulting from step b) (with as starting material the (semi-)refined alginates), from 2 to 50 molar equivalents of an alcohol of formula R'OH, as defined above, and advantageously or preferably 4 molar equivalents. The trans-esterification and trans-glycosylation reactions are then continued by making it possible to recycle the short-chain alcohol ROH previously used for the formation of the composition rich in L-guluronic acid derivatives or in a mixture of derivatives of L-guluronic acid and of D-mannuronic acid. The reaction is carried out for from 1 hour to 24 hours at a temperature advantageously or preferably of 70° C. and under reduced pressure for the recycling of the abovementioned alcohol. The composition thus formed constitutes a product for use derived from L-guluronic acid and/or from D-mannuronic acid, such as a hydrotropic agent, a non-ionic detergent or an emulsifier.

The next steps subsequently differ depending on whether it is desired to obtain compositions (1) of alkyl(alkyl mannoside)uronates and/or of alkyl(alkyl guloside)uronates, or (2) of alkyl mannoside uronic acid and/or alkyl guloside uronic acid salts.

According to one particular embodiment, a step of neutralization d) of the reaction medium resulting from step c), once it has been brought back to ambient temperature and to atmospheric pressure, can be carried out in the presence (i) of water, and (ii) of a base $M(OH)_x$ in which M is an alkali metal or alkaline-earth metal and x is the valency. This step d) is carried out, for example, by introducing, into the reaction medium resulting from step c) (with as starting material the poly(oligo)guluronates, the oligoalginates), once it has been brought back to ambient temperature and to atmospheric pressure, from 0 to 19 molar equivalents of an aqueous solution containing a base of formula $M(OH)_x$ as defined above, and advantageously or preferably 2.2 equivalents of a 1N sodium hydroxide solution; from 100 to 1000 molar equivalents of water and advantageously or preferably 780 molar equivalents. This step d) is carried out, for example, by introducing, into the reaction medium resulting from step c) (with as starting material the (semi-)refined alginates), once it has been brought back to ambient temperature and to atmospheric pressure, from 0 to 19 molar equivalents of an aqueous solution containing a base of formula $M(OH)_x$ as defined above, and advantageously or preferably 1.65 equivalents of a 1N sodium hydroxide solution; from 100 to 1000 molar equivalents of water and advantageously or preferably 775 molar equivalents. Next, the whole mixture is heated at 80° C. with vigorous stirring for 15 min. Once the mixture has returned to ambient temperature, the aqueous phase is separated from the organic phase. The latter is finally dried by azeotropic distillation of the water using butanol. The excess of alcohol of formula R'OH present in the organic crude can be partially or totally removed by molecular distillation. After an optional purification by silica gel chromatography (97:3 then 96:4 then 90:10 $CH_2Cl_2$/MeOH), a mixture of products is obtained. By way of example, in the case of the use of oligoalginate, the molar composition is approximately: 30% alkyl(n-alkyl α-D-mannopyranosiduronate); 5% alkyl(n-alkyl α-D-mannofuranosiduronate); 10% n-alkyl α,β-D-mannofuranosiduromo-6,3-lactone; 25% alkyl (n-alkyl α,β-L-gulopyranosiduronate); 10% alkyl (n-alkyl β-L-gulofuranosiduronate); 20% n-alkyl α,β-L-gulofuranosiduromo-6,3-lactone. By way of example, in the case of the use of semi-refined alginate derived from *Laminaria digitata*, the weight composition is approximately: 60% n-alkyl D-mannuronate and L-guluronate derivatives, 15% n-alkyl L-fucose, 25% n-alkyl α,β-D-glucopyranose.

Some embodiments are also directed to a process for preparing a composition including (i) alkyl guloside uronic acid salts or (ii) a mixture of alkyl guloside uronic acid salts and alkyl mannoside uronic acid salts, the process including a reaction of saponification e) of the ester resulting from step c), in the presence (i) of a base M(OH)$_x$ in which M is an alkali metal or an alkaline-earth metal, and x is the valency, or (ii) of a base wherein each of $R_3$ to $R_6$ is independently a hydrogen atom, an alkyl having from 1 to 6 carbon atoms or a hydroxyalkyl having from 1 to 6 carbon atoms. Advantageously or preferably, the base is chosen from the group including or consisting of: sodium hydroxide, potassium hydroxide, aqueous ammonia or an alkyl(hydroxyalkyl)ammonium hydroxide. This ester saponification step e) is carried out, for example, by introducing, into the reaction medium resulting from step c) (with as starting material the poly(oligo)guluronates, the oligoalginates or the (semi-)refined alginates), from 0.5 to 10 equivalents, and advantageously or preferably 1 to 3 equivalents, of a base of formula M(OH)$_x$ as defined above. Advantageously or preferably, the base M(OH)$_x$ is sodium hydroxide, potassium hydroxide, aqueous ammonia or an alkyl(hydroxyalkyl)ammonium hydroxide. The ester saponification reaction is preferentially carried out at temperatures of between 0° C. and 100° C., and advantageously or preferably at 70° C., and for a period of from 15 min to several hours, and advantageously or preferably for one hour. At the end of the reaction, the water is then removed by freeze-drying or by azeotropic distillation with butanol. The excess alcohol of formula R'OH can be partially or totally removed by molecular distillation or by solid-liquid extraction with an organic solvent, advantageously or preferably by solid-liquid extraction with acetone. After an optional purification by silica gel chromatography, a mixture of products is obtained. By way of example, in the case of the use of oligoalginate, the molar composition is approximately: 30% sodium n-alkyl α-D-mannopyranosiduronate; 15% sodium n-alkyl α,β-D-mannofuranosiduronate; 25% sodium n-alkyl α,β-L-gulopyranosiduronate; 30% sodium n-alkyl α,β-L-gulofuranosiduronate. By way of example, in the case of the use of semi-refined alginate derived from Laminaria digitata, the weight composition is approximately: 45% sodium n-alkyl D-mannuronate and sodium n-alkyl L-guluronate derivatives, 20% n-alkyl L-fucose and 35% n-alkyl α,β-D-glucopyranose.

Some embodiments are also directed to a process for preparing a composition including (i) alkyl guloside uronic acids or (ii) a mixture of alkyl guloside uronic acids and of alkyl mannoside uronic acids, the process including a reaction of acidification f) of the salts resulting from step e) in the presence of an acid chosen from the group including or consisting of: hydrochloric acid, sulfuric acid, oxalic acid, a sulfonic acid or a sulfonic resin in its form. The inorganic salts can be removed by liquid-liquid extraction. This acidification reaction is carried out, for example, by bringing 1 equivalent of salts resulting from step e) into contact with 1 equivalent or more of an acid as defined above. By way of example, in the case of the use of oligoalginate as starting material, the molar composition is approximately: 30% n-alkyl α-D-mannopyranosiduronic; 15% n-alkyl α,β-D-mannofuranosiduronic; 25% n-alkyl α,β-L-gulopyranosiduronic; 30% n-alkyl α,β-L-gulofuranosidurono-6,3-lactone. By way of example, in the case of the use of semi-refined alginate derived from Laminaria digitata as starting material, the weight composition is approximately: 45% n-alkyl D-mannuronic and L-guluronic derivatives, 20% n-alkyl L-fucose, 35% n-alkyl α,β-D-glucopyranose.

Some embodiments are also directed to a composition obtained by a process according to some embodiments. Advantageously or preferably, the composition combines, in the form of monomers, derivatives of L-guluronic acid or of the two uronic acids (L-guluronic acid and D-mannuronic acid) derived from the same polysaccharide, and in some cases hexoses and pentoses derived from other polysaccharides present in the algal extract (cellulose, hemicellulose, laminarans, fucan: the case of semi-refined alginates).

Some embodiments are laso directed to the use of a composition according to some embodiments as a surfactant. Advantageously or preferably, the surfactant is chosen from dissolving agents, hydrotropic agents, wetting agents, foaming agents, emulsifiers and/or detergents.

Some embodiments are laos directed to a surfactant including a composition according to some embodiments. The surfactant can have the following properties:

| Number of carbon atoms of the lipophilic (alkyl) chain: | Surfactant comprising two lipophilic chains: alkyl(alkyl mannoside)uronates and/or alkyl(alkyl guloside)uronates | |
|---|---|---|
| between 1 and 6 | Hydrotropic and/or dissolving agents | |
| between 6 and 14 | Oil-in-water (O/W) emulsifiers | |
| between 16 and 22 | Water-in-oil (W/O) emulsifiers | |
| Number of carbon | Surfactant comprising one lipophilic chain: | |
| atoms of the lipophilic (alkyl) chain: | Alkyl mannoside uronic acid salts and/or alkyl guloside uronic acid salts | Alkyl mannoside uronic acids and/or alkyl guloside uronic acids |
| between 4 and 6 | Dissolving and/or hydrotropic agents | |
| between 6 and 10 | Wetting agents and/or detergents | |
| between 10 and 16 | Wetting agents and/or detergents | |
| between 16 and 22 | Emulsifiers | |

The process and the compositions of some embodiments satisfy the principle of "blue chemistry":

- by exclusively using biobased starting materials (alginates (refined or semi-refined, bacterial), oligoalginates, poly(oligo)guluronates, fatty or non-fatty alcohols) or biocompatible/biodegradable starting materials;
- by implementing methodology which makes it possible to control the reactivity both of the L-guluronic acid and of the D-mannuronic acid derived from poly(oligo) guluronates, from oligoalginates, from refined or semi-refined bacterial alginates, so as to exploit L-guluronic acid or the mixture of the two saccharides (L-guluronic acid and D-mannuronic acid) in order to obtain the corresponding surfactant compositions;
- by using conditions which allow and exploit the presence of other polysaccharides (in particular cellulose, hemicelluloses, laminarans, fucans) in addition to the alginate (e.g. semi-refined alginates), thus resulting in compositions which combine at the same time uronic (L-guluronic acid and D-mannuronic acid) derivatives, hexoses (in particular glucose, fucose) and pentoses (in particular xylose);
- by proposing reaction conditions without organic solvents other than the reactive alcohols, not producing waste (recycling of short-chain alcohols (n-butanol, etc.)) and using biodegradable reagents (methanesulfonic acid and the like);
- by carrying out all of the reactions according to a "one-pot" process without isolation or purification of the reaction intermediates;
- by using simple conditions for partial purification of the reaction crudes (removal of the residual salts and/or fatty alcohols) or for isolation of the surfactant compositions which make it possible to achieve the derived compounds and the compositions which have performance levels/characteristics appropriate for the market needs.

Thus, some embodiments make it possible both to reduce the production costs for the surfactant compositions and to propose new compositions which are entirely biobased (brown algae, alginates (refined or semi-refined, bacterial), oligoalginates, poly(oligo)guluronates) or biocompatible/biodegradable, with a low ecotoxicity, starting from plant resources of marine origin, with the objective of enhancing or improving their performance levels.

The process which is the subject of some embodiments makes it possible to produce compositions derived from L-guluronic acid or derived both from L-guluronic acid and from D-mannuronic acid and which can include non-ionic surfactants derived from hexose (in particular glucose, fucose) and from pentoses (in particular xylose). These compositions have very good surfactant properties which can have applications in particular in fields such as dissolving agents, wetting agents, detergents, foaming agents or emulsifiers. In particular, the possibility of obtaining compositions including or consisting of a mixture of anionic and non-ionic surfactants from the same starting material (e.g. semi-refined alginates) and according to a "one-pot" process, constitutes a considerable alternative to the formulations based on anionic and non-ionic surfactants produced independently of one another and originating from starting materials of different nature. Indeed, "one-pot" processes make it possible to obtain at the same time non-ionic and anionic surfactants directly from oligomers (oligoalginates) including or consisting of the two uronic acids, whole polymers (alginates) in refined or semi-refined form, or else from brown algae. They avoid recourse to monosaccharide forms as starting materials, thereby greatly simplifying the process and reducing the cost of the surfactant compositions.

It will be possible for other advantages to become further apparent to those of ordinary skill in the art on reading the examples below, illustrated by the appended figures, the examples being given by way of illustration.

DETAILED DESCRIPTION OF EXEMPLARY EMBODIMENTS

EXAMPLES

Figure 5:
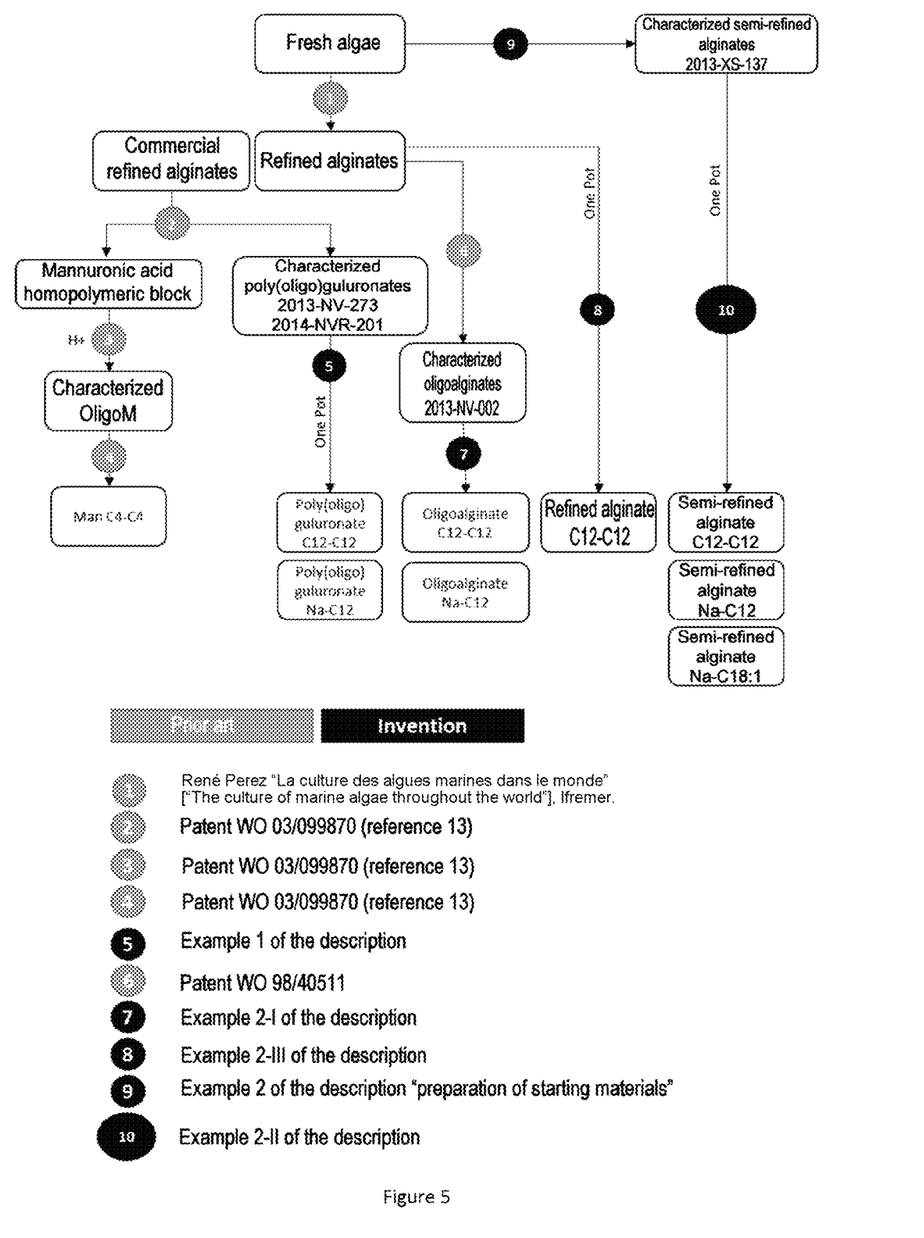
FIG. 5 represents the process for preparing compositions including alkyl(alkyl guloside)uronates of some embodiments starting from various algal starting materials, and related art preparation processes.

Example 1: Preparation of a Composition Including Alkyl(Alkyl Guloside)Uronates from Poly(Oligo)Guluronates C12-C12 Poly(Oligo)Guluronate (FIG. 5)

2013-NV-273: poly(oligo)guluronate obtained according to the process of international application WO 03/099870 [13]

| Description | Method | Result | Units |
|---|---|---|---|
| Solids | Constant weight at 103° C. | 83.9 | % dry/crude |
| Mineral matter | 12 h, 550° C. | 25.0 | % dry/crude |
| Ratio (M/G) | By calculation, proton NMR | 0.2 | |
| DP | By calculation | 21.5 | |

The poly(oligo)guluronate 2013-NV-273 (500 mg, 1.79 mmol $CO_2^-$, 1 eq) was dispersed in water (0.9 ml) and butanol (25 ml, 273 mmol, 153 eq). The 70% methanesulfonic acid solution (401 µl, 3.94 mmol, 2.2 eq) was added and the mixture was refluxed with vigorous stirring. The water formed in the medium was gradually removed by azeotropic distillation. At 7 h of reaction, the mixture was cooled to ambient temperature.

Dodecanol (1.6 ml, 7.2 mmol, 4 eq) and the 70% methanesulfonic acid solution (182 µl, 1.79 mmol, 1 eq) were added. The mixture was stirred at 70° C. under reduced pressure (up to 5 mbar).

Once the butanol had been completely removed (1.25 h), the mixture was neutralized by adding 1M NaOH (4.5 ml) and water (20 ml) at ambient temperature and atmospheric pressure. The whole mixture was heated at 80° C. with vigorous stirring for 15 min. Once the mixture had returned to ambient temperature, the aqueous phase was separated from the organic phase. The latter was finally dried by azeotropic distillation of the water using butanol. It was possible to partially or totally remove the excess dodecanol present in the organic crude by molecular distillation.

After an optional purification by silica gel chromatography (97:3 ($CH_2Cl_2$/MeOH), a mixture of products was obtained (270 mg), the molar composition of which is: 9% dodecyl (n-dodecyl α-D-mannopyranosiduronate); 2% dodecyl (n-dodecyl α-D-mannofuranosiduronate); 5% n-dodecyl β-D-mannofuranosidurono-6,3-lactone; 15% dodecyl (n-dodecyl α-L-gulopyranosiduronate); 25% dodecyl (n-dodecyl β-L-gulopyranosiduronate); 12% dodecyl (n-dodecyl β-L-gulofuranosiduronate); 21% n-dodecyl α-L-gulofuranosidurono-6,3-lactone; 11% n-dodecyl β-L-gulofuranosidurono-6,3-lactone.

Na—C12 Poly(Oligo)Guluronate (FIG. 5)

2014-NVR-201: poly(oligo)guluronate obtained according to the process of international application WO 03/099870 [13]

| Description | Method | Result | Units |
|---|---|---|---|
| Solids | Constant weight at 103° C. | 100.0 | % dry/crude |
| Mineral matter | 12 h, 550° C. | 26.3 | % dry/crude |
| Ratio (M/G) | By calculation, proton NMR | 0.039 | |
| DP | By calculation | 30 | |

The poly(oligo)guluronate 2014-NVR-201 (1.000 g, 4,2 mmol $CO_2^-$, 1 eq) was dispersed in water (3.0 ml) and butanol (58 ml, 634 mmol, 151 eq). The 70% methanesulfonic acid solution (940 μl, 9.24 mmol, 2.2 eq) was added and the mixture was refluxed with vigorous stirring. The water formed in the medium was gradually removed by azeotropic distillation. At 7 h of reaction, the mixture was cooled to ambient temperature.

Dodecanol (3.7 ml, 16.6 mmol, 4 eq) and the 70% methanesulfonic acid solution (423 μl, 4.16 mmol, 1 eq) were added. The mixture was stirred at 70° C. under reduced pressure (up to 5 mbar).

Once the butanol had been completely removed (1.25 h), a 0.4M NaOH solution (37 ml) was added and the mixture was left to stir vigorously at 70° C. for 1 h. The water was then removed by freeze-drying or by azeotropic distillation with butanol. It was possible to partially or totally remove the excess dodecanol present in the crude product by solid-liquid extraction with acetone.

At the end of this treatment, a mixture of products was obtained (2.981 g), the percentage of mineral matter of which is 38.5%/crude.

H—C12 Poly(Oligo)Guluronate

A portion of this mixture of products above (816 mg) was dissolved in ice-cold water (15 ml), then a 1M hydrochloric acid solution (2.0 ml) was added. The aqueous solution was extracted with ethyl acetate (3×10 ml). The organic phases were combined and washed with a saturated NaCl solution (20 ml). The organic phase was dried with $MgSO_4$ and then concentrated under vacuum. A mixture of products was obtained (195 mg), the molar composition of which is: 21% n-dodecyl α-D-mannopyranosiduronic; 11% n-dodecyl β-L-gulopyranosiduronic; 34% n-dodecyl α-L-gulofuranosidurono-6,3-lactone; 34% n-dodecyl β-L-gulofuranosidurono-6,3-lactone.

Example 2: Preparation of a Composition Including a Mixture of Alkyl(Alkyl Guloside)Uronates and of Alkyl(Alkyl Mannoside)Uronates Preparation of the starting materials: The alginate extraction processes are conventionally used at CEVA [Centre for Study and Exploitation of Algae] (Rene Perez "La culture des algues marines dans le monde" ["Cultivation of marine algae throughout the world"], Ifremer: see FIG. 5). They involve acid leaching of fresh or dry algae (washing of the harvested algae with sea water, depigmentation in formol, milling, extraction with 0.2N sulfuric acid at ambient temperature, draining and rinsing of the leached algae with distilled water), followed by dissolution of the sodium alginates by increasing the pH of the medium and then solid/liquid separation in order to remove the algal residues (addition of a 1.5% $Na_2CO_3$ solution to 50 g, on a dry basis, of leached algal material according to a dry alga/1.5% $Na_2CO_3$ solution ratio of 0.025, stirring in an IKA reactor for 3 h at 55° C., cooling in a water bath with a few ice cubes in order to prevent excessive temperature differences, centrifugation for 5 minutes at 6000 rpm, solid/liquid separation). At this stage, the liquid fraction can be frozen and freeze-dried and constitutes the semi-refined alginates in the form of sodium alginates. In order to obtain refined alginates, a purification is introduced into the preceding steps. After separation of the algal residues, the latter purification step includes or consists of precipitation of the alginic acid by reducing the pH, followed by several washes with acidic water in order to remove the co-products. Increasing the pH with $Na_2CO_3$ makes it possible to again dissolve the sodium alginates while limiting the salts, compared with the use of sodium hydroxide. Finally, a final step of freezing and then freeze-drying makes it possible to achieve the final product. In order to obtain the saturated or unsaturated oligoalginates, the alginate solution is treated enzymatically or with acid in order to reduce the degree of polymerization of the alginates from 20 to 3.

I—Starting from Oligoalginates

C12-C12 Oligoalginate (FIG. 5)

2013-NV-002: oligoalginate obtained according to the process described in Example 2 and/or obtained according to the process of international application WO 98/40511 [14].

| Description | Method | Result | Units |
|---|---|---|---|
| Solids | Constant weight at 103° C. | 90.1 | % dry/crude |
| Mineral matter | 12 h, 550° C. | 44.3 | % dry/dry |
| Ratio (M/G) | By calculation, proton NMR | 1.4 | |
| DP | By calculation | 12.7 | |

The oligoalginate 2013-NV-002 (500 mg, 1.42 mmol $CO_2^-$, 1 eq) was dispersed in water (0.9 ml) and butanol (19.5 ml, 213 mmol, 150 eq). The 70% methanesulfonic acid solution (318 μl, 3.12 mmol, 2.2 eq) was added and the mixture was refluxed with vigorous stirring. The water formed in the medium was gradually removed by azeotropic distillation. At 7 h of reaction, the mixture was cooled to ambient temperature.

Dodecanol (1.3 ml, 5.8 mmol, 4 eq) and the 70% methanesulfonic acid solution (145 μl, 1.43 mmol, 1 eq) were added. The mixture was stirred at 70° C. under reduced pressure (up to 5 mbar).

Once the butanol had been completely removed (1.25 h), the mixture was neutralized by adding 1M NaOH (3.2 ml) and water (20 ml) at ambient temperature and atmospheric pressure. The whole mixture was heated at 80° C. with vigorous stirring for 15 min. Once the mixture had returned to ambient temperature, the aqueous phase was separated from the organic phase. The latter was finally dried by azeotropic distillation of the water using butanol. It was possible to partially or totally remove the excess dodecanol present in the organic crude by molecular distillation.

After an optional purification by silica gel chromatography (97:3 $CH_2Cl_2$/MeOH), a mixture of products was obtained (231 mg), the molar composition of which is: 29% dodecyl (n-dodecyl α-D-mannopyranosiduronate); 6% dodecyl (n-dodecyl α-D-mannofuranosiduronate); 12% n-dodecyl α,β-D-mannofuranosidurono-6,3-lactone; 23% dodecyl (n-dodecyl α,β-L-gulopyranosiduronate); 9% dodecyl (n-dodecyl β-L-gulofuranosiduronate); 21% n-dodecyl α,β-L-gulofuranosidurono-6,3-lactone.

Na—C12 Oligoalginate (FIG. 5)

The oligoalginate 2013-NV-002 (1.000 g, 2.84 mmol $CO_2^{-1}$, 1 eq) was dispersed in water (2.0 ml) and butanol (39 ml, 426 mmol, 150 eq). The 70% methanesulfonic acid solution (634 µl, 6.24 mmol, 2.2 eq) was added and the mixture was refluxed with vigorous stirring. The water formed in the medium was gradually removed by azeotropic distillation. At 7 h of reaction, the mixture was cooled to ambient temperature.

Dodecanol (2.5 ml, 11.2 mmol, 4 eq) and the 70% methanesulfonic acid solution (290 µl, 2.85 mmol, 1 eq) were added. The mixture was stirred at 70° C. under reduced pressure (up to 5 mbar).

Once the butanol had been completely removed (1.25 h), a 0.4M NaOH solution (25 ml) was added and the mixture was left to stir vigorously at 70° C. for 1 h. The water was then removed by freeze-drying or by azeotropic distillation with butanol. It was possible to partially or totally remove the excess dodecanol present in the crude product by solid-liquid extraction with acetone.

At the end of this treatment, a mixture of products was obtained (2.532 g), the percentage of mineral matter of which is 41.8%/crude.

H—C12 Oligoalginate

A portion of this mixture of products above (837 mg) was dissolved in ice-cold water (15 ml) and then a 1M hydrochloric acid solution (2.0 ml) was added. The aqueous solution was extracted with ethyl acetate (3×10 ml). The organic phases were combined and washed with a saturated NaCl solution (20 ml). The organic phase was dried with $MgSO_4$ and then concentrated under vacuum. A mixture of products was obtained (251 mg), the molar composition of which is: 32% n-dodecyl α-D-mannopyranosiduronic; 13% n-dodecyl β-L-gulopyranosiduronic; 29% n-dodecyl α-L-gulofuranosidurono-6,3-lactone; 26% n-dodecyl β-L-gulofuranosidurono-6,3-lactone.

II—Starting from Semi-Refined Alginate

C12-C12 Semi-Refined Alginate (FIG. 5)

2013-XS-137: the semi-refined alginate derived from *Laminaria digitata* obtained in accordance with the process described in Example 2.

| Description | Method | Result | Units |
|---|---|---|---|
| Solids | Constant weight at 103° C. | 94.9 | % dry/crude |
| Mineral matter | 12 h, 550° C. | 47.0 | % dry/dry |
| Mannuronic and guluronic acid content | Methanolysis | 29.2 | % dry/dry |

| Description | Method | Result | Units |
|---|---|---|---|
| Glucose content | Methanolysis | 10.9 | % dry/dry |
| Xylose content | Methanolysis | <0.5 | % dry/dry |
| Fucose content | Methanolysis | 2.1 | % dry/dry |
| Ratio (M/G) | By calculation, proton NMR | 2.6 | |

The semi-refined alginate 2013-XS-137 derived from *Laminaria digitata* (1.000 g, 2.15 mmol sugar units, 1 eq) was dispersed in water (30 ml) and the 70% methanesulfonic acid solution (1.09 ml, 10.7 mmol, 5 eq) was added. The mixture was refluxed with vigorous stirring. At 8 h of reaction, butanol (30 ml, 328 mmol, 153 eq) was added and the mixture was left at reflux with vigorous stirring. The water present in the medium was gradually removed by azeotropic distillation.

After a further 15 h of reaction, and once the mixture had returned to ambient temperature, dodecanol (1.92 ml, 8.6 mmol, 4 eq) was added. The mixture was stirred at 70° C. under reduced pressure (up to 5 mbar).

Once the butanol had been completely removed (1.25 h), the mixture was neutralized by adding 1M NaOH (3.55 ml) and water (30 ml) at ambient temperature and atmospheric pressure. The whole mixture was heated at 80° C. with vigorous stirring for 15 min. Once the mixture had returned to ambient temperature, the aqueous phase was separated from the organic phase. The latter was then washed with water (30 ml) by stirring at 80° C. for 15 min. The organic phase was recovered and then dried by azeotropic distillation of the water using butanol. It was possible to partially or totally remove the excess dodecanol present in the crude product by molecular distillation.

After an optional purification by silica gel chromatography (97:3 then 96:4 then 90:10 $CH_2Cl_2$/MeOH), a mixture of products was obtained (377 mg), the weight composition of which is: dodecyl (n-dodecyl α-D-mannofuranosiduronate), n-dodecyl α,β-D-mannofuranosidurono-6,3-lactone, dodecyl (n-dodecyl β-L-gulofuranosiduronate) and n-dodecyl α,β-L-gulofuranosidurono-6,3-lactone 35%, dodecyl (n-dodecyl α-D-mannopyranosiduronate) and dodecyl (n-dodecyl gulopyranosiduronate) 25%, 14% n-dodecyl L-fucose, 26% n-dodecyl α,β-D-glucopyranose.

Na—C12 Semi-Refined Alginate (FIG. 5)

The semi-refined alginate 2013-XS-137 derived from *Laminaria digitata* (2.000 g, 4.3 mmol sugar units, 1 eq) was dispersed in water (60 ml) and the 70% methanesulfonic acid solution (2.19 ml, 21.5 mmol, 5 eq) was added. The mixture was refluxed with vigorous stirring. At 8 h of reaction, butanol (60 ml, 656 mmol, 152 eq) was added and the mixture was left at reflux with vigorous stirring. The water present in the medium was gradually removed by azeotropic distillation.

After a further 15 h of reaction, and once the mixture had returned to ambient temperature, dodecanol (3.8 ml, 17 mmol, 4 eq) was added. The mixture was stirred at 70° C. under reduced pressure (up to 5 mbar).

Once the butanol had been completely removed (1.25 h), a 0.2M NaOH solution (60 ml) was added and the mixture was left to stir vigorously at 70° C. for 1 h. The water was then removed by freeze-drying or by azeotropic distillation with butanol. It was possible to partially or totally remove the excess dodecanol present in the crude product by solid-liquid extraction with acetone.

At the end of this treatment, a mixture of products was obtained (3.592 g), the percentage of mineral matter of which is 42.4%/crude.

H—C12 Semi-Refined Alginate

A portion of this mixture of products above (1.081 g) was dissolved in ice-cold water (15 ml) and then a 1M hydrochloric acid solution (2.0 ml) was added. The aqueous solution was extracted with ethyl acetate (3×10 ml). The organic phases were combined and washed with a saturated NaCl solution (20 ml). The organic phase was dried with $MgSO_4$ and then concentrated under vacuum. A mixture of products was obtained (138 mg), the weight composition of which is: n-dodecyl D-mannuronic and L-guluronic derivatives 67%, n-dodecyl L-fucose and n-dodecyl glucopyranose 33%.

Na—C18:1 Semi-Refined Alginate (FIG. 5)

The semi-refined alginate 2013-XS-137 derived from *Laminaria digitata* (2.000 g, 4.3 mmol sugar units, 1 eq) was dispersed in water (60 ml) and the 70% methanesulfonic acid solution (2.19 ml, 21.5 mmol, 5 eq) was added. The mixture was refluxed with vigorous stirring. At 8 h of reaction, butanol (60 ml, 656 mmol, 152 eq) was added and the mixture was left at reflux with vigorous stirring. The water present in the medium was gradually removed by azeotropic distillation. After a further 15 h of reaction, and once the mixture had returned to ambient temperature, oleyl alcohol (5.4 ml, 17 mmol, 4 eq) was added. The mixture was stirred at 70° C. under reduced pressure (up to 5 mbar). Once the butanol had been completely removed (1.25 h), a 0.2M NaOH solution (60 ml) was added and the mixture was left to stir vigorously at 70° C. for 1 h. The water was then removed by freeze-drying or by azeotropic distillation with butanol. It was possible to partially or totally remove the excess oleyl alcohol present in the crude product by solid-liquid extraction with acetone. At the end of this treatment, a mixture of products was obtained (3.418 g), the percentage of mineral matter of which is 44.1%/crude.

III—Starting from Refined Alginate

C12-C12 Refined Alginate (FIG. 5)

2013-NV-277: refined alginate derived from *Laminaria digitata* obtained according to the process described in Example 2.

| Description | Method | Result | Units |
|---|---|---|---|
| Solids | Constant weight at 103° C. | 94.2 | % dry/crude |
| Mineral matter | 12 h, 550° C. | 37.2 | % dry/dry |
| Ratio (M/G) | By calculation, proton NMR | 2.6 | |
| DP | By calculation | 362 | |

The refined alginate 2013-NV-277 derived from *Laminaria digitata* (1.000 g, 2.38 mmol $CO_2^-$, 1 eq) was dispersed in water (30 ml) and the 70% methanesulfonic acid solution (1.21 ml, 11.9 mmol, 5 eq) was added. The mixture was refluxed with vigorous stirring. At 8 h of reaction, butanol (33 ml, 361 mmol, 152 eq) was added and the mixture was left at reflux with vigorous stirring. The water present in the medium was gradually removed by azeotropic distillation. After a further 15 h of reaction, and once the mixture had returned to ambient temperature, dodecanol (2.12 ml, 9.5 mmol, 4 eq) was added. The mixture was stirred at 70° C. under reduced pressure (up to 5 mbar). Once the butanol had been completely removed (1.25 h), the mixture was neutralized by adding 1M NaOH (3.95 ml) and water (30 ml) at ambient temperature and atmospheric pressure. The whole mixture was heated at 80° C. with vigorous stirring for 15 min. Once the mixture had returned to ambient temperature, the aqueous phase was separated from the organic phase. The latter was finally dried by azeotropic distillation of the water using butanol. It was possible to partially or totally remove the excess dodecanol present in the organic crude by molecular distillation. After an optional purification by silica gel chromatography (97:3 $CH_2Cl_2$/MeOH), a mixture of products was obtained (387 mg), the molar composition of which is: 8% dodecyl (n-dodecyl α-D-mannofuranosiduronate), 4% n-dodecyl β-D-mannofuranosidurono-6,3-lactone, 11% dodecyl (n-dodecyl β-L-gulofuranosiduronate), 4% n-dodecyl α-L-gulofuranosidurono-6,3-lactone, 7% n-dodecyl β-L-gulofuranosidurono-6,3-lactone, 48% dodecyl (n-dodecyl α-D-mannopyranosiduronate), 5% dodecyl (n-dodecyl α-L-gulopyranosiduronate), 13% dodecyl (n-dodecyl β-L-gulopyranosiduronate).

Example 3: Tensiometric Measurements of the Compositions of Some Embodiments

Interfacial Tension

The interfacial tension measurements were carried out using a Krüss tensiometer with a horizontally suspended platinum ring. Before each measurement, the ring was meticulously cleaned and flame-dried. The sample bucket is a cylindrical glass container placed in a thermoregulated chamber. The sample solutions were prepared with sunflower oil. The interfacial tension measurements were carried out between Milli-Q water and the sample solutions in oil.

The various batches of C12-C12 derivative surfactants obtained at the end of the purification by chromatography were characterized by interfacial tension measurements between water and sunflower oil.

Figure 1:
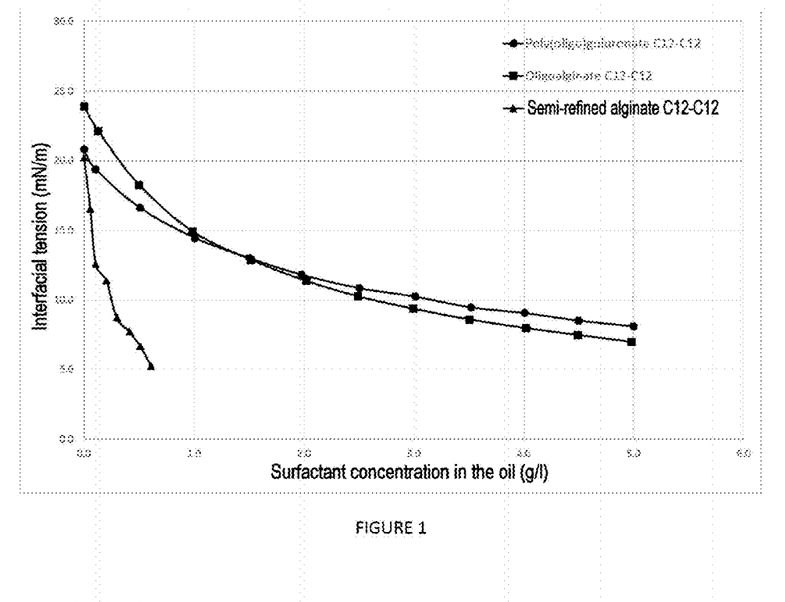
FIG. 1 represents the tensiometric measurements carried out on the C12-C12 derivatives derived from poly(oligo) guluronate, from oligoalginate and from semi-refined alginate.

The results represented in FIG. 1 show that the interfacial tension is clearly decreased regardless of the surfactant batch. However, the batch obtained from semi-refined alginate is the one which makes it possible to most efficiently reduce the tension. Indeed, it makes it possible to achieve the same tension values at concentrations that are 10 times lower; for example, 7.0 mN/m at 0.5 g/l instead of 5.0 g/l.

Surface Tension

The surface tension measurements were carried out using a Krüss tensiometer with a horizontally suspended platinum ring. Before each measurement, the ring was meticulously cleaned and flame-dried. The sample bucket is a conical PTFE container placed in a thermoregulated chamber. The sample solutions were prepared with Milli-Q water and continually stirred using a magnetic bar before each measurement.

The various batches of Na—C12 derivative surfactants obtained at the end of the solid-liquid extraction were characterized by surface tension measurements.

Figure 2:
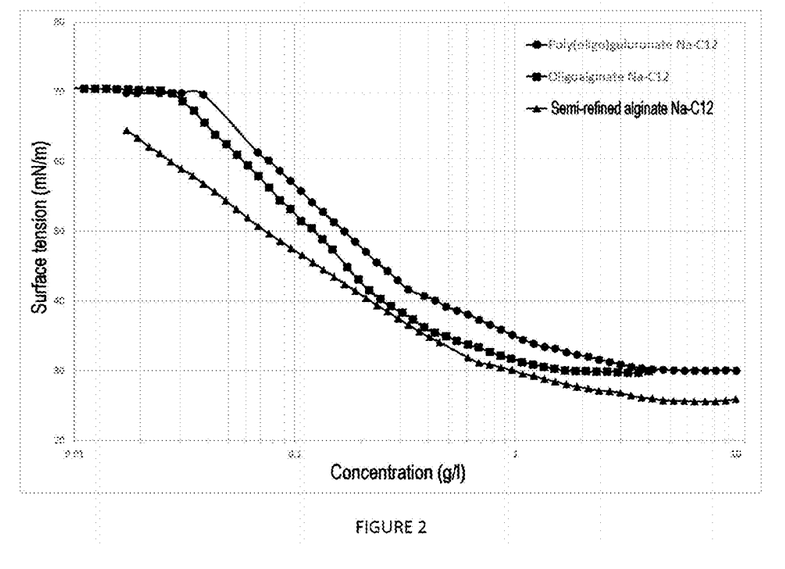
FIG. 2 represents the tensiometric measurements carried out on the Na—C12 derivatives derived from poly(oligo) guluronate, from oligoalginate and from semi-refined alginate.

The results represented in FIG. 2 show first of all that all the batches of surfactants make it possible to efficiently reduce the surface tension of the water, since values of between 25 and 30 mN/m were measured at the respective critical micelle concentrations (CMCs). However, very different CMC values are obtained depending on the batches. Specifically, the batch derived from oligoalginate has the lowest value (1.9 g/l), whereas that obtained from poly(oligo)guluronate has the highest value (5.0 g/l). The batch derived from semi-refined alginate (*L. digitata*) has an intermediate CMC value: 4.7 g/l. It is, however, possible to note that the latter is the one which makes it possible to most efficiently reduce the surface tension, since a tension of 25.7 mN/m was measured at the CMC. It is also important to note that, for all the concentration values, the lowest surface tension values were measured with the batch obtained from semi-refined alginate.

Figure 3:
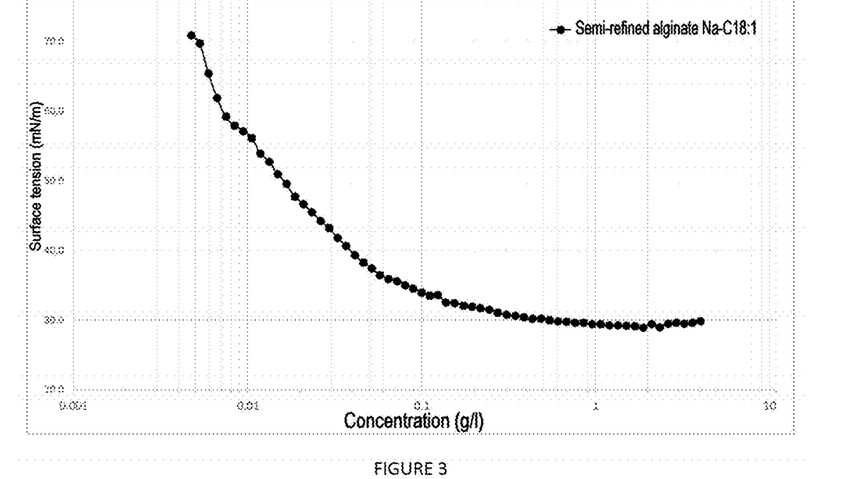
FIG. 3 represents the tensiometric measurements carried out on the Na—C18:1 derivatives derived from semi-refined alginate.

The batch of Na—C18:1 derivative surfactants, derived from semi-refined alginate, obtained at the end of the solid-liquid extraction was characterized by surface tension measurements (FIG. 3).

The results represented in FIG. 3 show that the batch makes it possible to efficiently reduce the surface tension. A CMC of 0.55 g/l and a $\gamma_{CMC}$ of 30 mN/m were measured.

Figure 4:
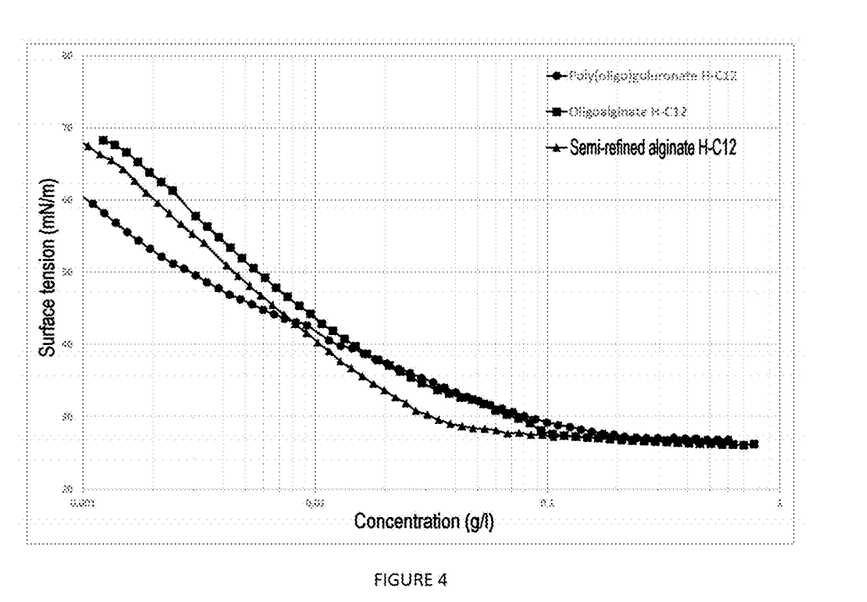
FIG. 4 represents the tensiometric measurements carried out on the H—C12 derivatives derived from poly(oligo) guluronate, from oligoalginate and from semi-refined alginate.

The various batches of H—C12 derivative surfactants obtained after acidification of the Na—C12 derivatives and removal of the inorganic salts were characterized by surface tension measurements (FIG. 4).

The results represented in FIG. 4 show first of all that all the batches of surfactants make it possible to efficiently reduce the surface tension of water since values of less than 30 mN/m were measured at the CMCs. The batch obtained from poly(oligo)guluronate has a CMC of 0.12 g/l with a $\gamma_{CMC}$ of 28.8 mN/m. The results obtained with the batch derived from oligoalginate are slightly better, since the CMC is 0.11 g/l and the $\gamma_{CMC}$ is 27.6 mN/m. Finally, the batch obtained from semi-refined alginate (*L. digitata*) makes it possible to obtain the lowest CMC with a value of 0.04 g/l and a vac of 29 mN/m. It is also important to note that, for the concentrations of less than 0.008 g/l, the lowest surface tension values were measured with the batch obtained from poly(oligo)guluronate.

REFERENCE LIST

1—"Sugar-based Surfactants : fundamentals and applications", Surfactant science series vol.143, Ed. C. Carnero Ruiz, CRC Press Taylor & Francis Group, 2009 (ISBN 978-1-4200-5166-7)
2—Behler et al., in Proceedings 6th World Surfactant Congress, CESIO June, Berlin, 2004
3—Patent EP 0532370
4—U.S. Pat. No. 5,312,907
5—Patent application FR 2717177
6—International application WO 93/02092
7—International application WO 98/12228
8—U.S. Pat. No. 5,147,861
9—Benvegnu et al., Topics in Current Chemistry, 294: 143-164, 2010
10—Roussel et al., Eur. J. Org. Chem., 3085-3094, 2005
11—Patent application FR 02/840306
12—International application WO 03/104248
13—International application WO 03/099870
14—International application WO 09/134368
15—International application WO 98/40511

The invention claimed is:

1. A process for preparing a composition, the process comprising:
(i) alkyl(alkyl guloside)uronates of formulae (Ia), (Ib) and (Ic), wherein:

(Ia)

(Ib)

(Ic)

or
(ii) a mixture of alkyl(alkyl guloside)uronates of formulae (Ia), (Ib) and (Ic) and of alkyl(alkyl mannoside)uronates of formulae (IIa), (IIb) and (IIc):

(IIa)

(IIb)

(IIc)

wherein
$R_1$ is a linear or branched, saturated or unsaturated alkyl chain having from 2 to 22 carbon atoms;
$R_2$ is a hydrogen atom, $R_1$ is an alkali metal atom, an alkaline-earth metal atom, or a quaternary ammonium group of formula (III):

(III)

wherein
each of $R_3$ to $R_6$ is independently a hydrogen atom, an alkyl having from 1 to 6 carbon atoms or a hydroxyalkyl having from 1 to 6 carbon atoms, and the process further includes:

a) performing hydrolysis of poly(oligo)guluronates, of oligoalginates, of alginates and/or brown algae;
b) performing esterification and glycosylation of the hydrolysate resulting from the hydrolysis with a linear or branched, saturated or unsaturated alcohol of formula ROH, having from 1 to 4 carbon atoms;
c) performing trans-esterification and trans-glycosylation of the reaction medium resulting from the esterification and glycosylation with a linear or branched, saturated or unsaturated alcohol of formula R'OH having from 2 to 22 carbon atoms; and
d) performing neutralizating the reaction medium resulting from the trans-esterification and trans-glycosylation the presence of water and of a base $M(OH)_x$ in which M is an alkali metal or alkaline-earth metal, and x is the valency.

2. The process as claimed in claim 1, wherein the hydrolysis is carried out in the presence of:
   (i) water and/or of an ionic solvent and/or of a eutectic solvent, and
   (ii) and acid catalyst.

3. The process as claimed in claim 2, wherein the acid catalyst is selected from the group consisting of: hydrochloric acid, sulfuric acid, an alkyl sulfuric acid, a sulfonic acid, an alkylsulfonic acid or an alkyl sulfosuccinate, perhalohydric acids, metals, oxides thereof or salts thereof such as halides thereof.

4. The process as claimed in claim 3, wherein the acid catalyst is methanesulfonic acid.

5. The process as claimed in claim 1, wherein the alcohol ROH is n-butanol.

6. The process as claimed in claim 1, wherein the alcohol ROH is selected from the group consisting of dodecanol and oleyl alcohol.

7. The process as claimed in claim 1, wherein the esterification and glycosylation is carried out at atmospheric pressure and at the boiling point of water or of the azeotrope formed with the alcohol ROH.

8. The process as claimed in claim 1, wherein the trans-esterification and trans-glycosylation is carried out at 70° C. under reduced pressure in order to recycle the alcohol ROH.

9. A process for preparing a composition that includes (i) alkyl guloside uronic acid salts or (ii) a mixture of alkyl guloside uronic acid salts and of alkyl mannoside uronic acid salts, comprising:
   the process of claim 1; and
   e) saponification of the ester resulting from the trans-esterification and trans-glycosylation.

10. The process as claimed in claim 9, wherein the saponification is carried out in the presence of:
    (i) a base $M(OH)_x$ in which M is an alkali or alkaline-earth metal and x is the valency, or
    (ii) a bae of the formula wherein each of $R_3$ to $R_6$ is independently a hydrogen atom, an alkyl having from 1 to 6 carbon atoms or a hydroxyalkyl having from 1 to 6 carbon atoms.

11. The process as claimed in claim 10, wherein the base is selected from the group consisting of: sodium hydroxide, potassium hydroxide, aqueous ammonia or an alkyl(hydroxyalkyl)ammonium hydroxide.

12. The process as claimed in claim 10, wherein the saponification is carried out at a temperature of from 0 to 100° C.

13. A process for preparing a composition that includes (i) alkyl guloside uronic acids or (ii) a mixture of alkyl guloside uronic acids and alkyl mannoside uronic acids, the process comprising:
    the process of claim 9; and
    f) acidification of the salts resulting from the saponification.

14. The process as claimed in claim 13, wherein the acidification is carried out in the presence of an acid selected from the group consisting of: hydrochloric acid, sulfuric acid, a sulfonic acid or a sulfonic resin in its $H^+$ form.

15. A composition obtained by the process as claimed in claim 1.

16. The use of a composition as claimed in claim 15 as a surfactant.

17. The use as claimed in claim 16, wherein the surfactant is selected from the group consisting of dissolving agents, hydrotropic agents, wetting agents, foaming agents, emulsifiers and/or detergents.

18. A surfactant, comprising:
    the composition as claimed in claim 15.

19. The process as claimed in claim 2, wherein the alcohol ROH is n-butanol.

20. The process as claimed in claim 11, wherein the saponification is carried out at a temperature of from 0 to 100° C.

* * * * *

UNITED STATES PATENT AND TRADEMARK OFFICE
CERTIFICATE OF CORRECTION

PATENT NO. : 10,544,180 B2
APPLICATION NO. : 16/061181
DATED : January 28, 2020
INVENTOR(S) : Thierry Benvegnu et al.

Page 1 of 1

It is certified that error appears in the above-identified patent and that said Letters Patent is hereby corrected as shown below:

In the Claims

In Column 19, Lines 54 and 55, replace "composition, the process comprising:" with --composition that includes:--

In Column 19, Line 57, replace "(IC), wherein" with --(IC)--

In Column 20, Line 54, replace "atoms;" with --atoms; and--

In Column 20, Lines 66 and 67, replace "process further includes:" with --process includes:--

In Column 21, Line 12, replace "neutralizating" with --neutralization of--

In Column 21, Line 14, replace "the presence" with --in the presense--

In Column 21, Line 20, replace "of an" with --an--

In Column 21, Line 20, replace "of a" with --a--

In Column 21, Line 22, replace "and" with --an--

In Column 21, Line 33, replace "ROH" with --R'OH--

In Column 22, Line 5, replace "bae" with --base--

Signed and Sealed this
Second Day of June, 2020

Andrei Iancu
*Director of the United States Patent and Trademark Office*